US005460826A

United States Patent [19]
Merrill et al.

[11] Patent Number: 5,460,826
[45] Date of Patent: Oct. 24, 1995

[54] MORPHINE THERAPY

[75] Inventors: Sonya Merrill, San Jose; Atul D. Ayer, Palo Alto; Paul Hwang, Campbell; Anthony L. Kuczynski, Mt. View, all of Calif.

[73] Assignee: Alza Corporation, Palo Alto, Calif.

[21] Appl. No.: 266,075

[22] Filed: Jun. 27, 1994

[51] Int. Cl.⁶ .............................. A61K 9/20; A61K 9/22; A61K 9/24
[52] U.S. Cl. .................. 424/470; 424/464; 424/468; 424/469; 424/472
[58] Field of Search ..................... 424/457–461, 424/464, 465, 468, 474, 469, 470, 472, 473

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,111,201 | 9/1978 | Theeuwes et al. | 128/260 |
| 4,111,202 | 9/1978 | Theeuwes | 128/260 |
| 4,327,725 | 5/1982 | Cortese et al. | 128/260 |
| 4,464,378 | 8/1984 | Hussain | 424/260 |
| 4,576,604 | 3/1986 | Guittard et al. | 604/890 |
| 4,612,008 | 9/1986 | Wong et al. | 604/892 |
| 4,968,507 | 11/1990 | Zentner | 424/465 |
| 5,021,053 | 6/1991 | Barclay et al. | 604/892 |
| 5,128,143 | 7/1992 | Baichwal | 424/464 |
| 5,186,942 | 2/1993 | Deters | 424/473 |

*Primary Examiner*—Goliamudi S. Kishore
*Attorney, Agent, or Firm*—Paul L. Sabatine; Felissa H. Cagan; Richard T. Ito

[57] ABSTRACT

A bilayer comprising a morphine layer of morphine, poly(alkylene oxide) and poly(vinylpyrrolidone); and an expandable contacting layer of coated granules of a higher molecular weight poly(alkylene oxide) and a hydroxyalkylcellulose, which bilayer is disclosed for morphine therapy. A method is disclosed for using the bilayer composition.

3 Claims, No Drawings

MORPHINE THERAPY

FIELD OF THE INVENTION

This invention pertains to a novel therapeutic composition of matter comprising morphine. This invention also concerns a novel dosage form comprising morphine. This invention additionally relates to a method of administering the therapeutic composition comprising morphine to produce an analgesic effect. The invention further relates to a method of administering the dosage form for delivering morphine to produce an analgesic effect.

BACKGROUND OF THE INVENTION

Morphine is a potent narcotic analgesic which is principally used to relieve pain. Morphine is used also in the management of dyspnea of heart failure, in pulmonary edema and cough, as a sedative, and in the control of diarrhea. Morphine most significant actions are analgesic, hypnosis, respiratory depression, central nervous system depressant effects, and as a local anesthetic. Morphine is administered effectively by injection, but a pharmaceutically acceptable material means for administering morphine orally as an analgesic, as an adjunct to anesthesia, as an antitussine, and a nonspecific antidiarrheal therapy appears to be lacking in the pharmaceutical and medical arts.

SUMMARY OF THE INVENTION

In view of the foregoing, it is apparent that a serious need exists for an improved delivery of morphine for its therapeutic effects. Thus, it is an object of the present invention to provide a novel therapeutic composition comprising morphine, and a novel dosage form comprising morphine, which therapeutic composition, or dosage form in both inventions provides a novel method of administering morphine for its intended therapy. The invention provides a novel and unique means of morphine administration when compared to intramuscular, subcutaneous, and intravenous administration.

DETAILED DESCRIPTION OF THE INVENTION

The drug morphine as embraced by this invention comprises (5α, 6α)-7,8-didehydro-4,5-epoxy-17-methylmorphinan-3,6-diol. Representative of morphines for this invention comprise a member selected from the group consisting of morphine base, morphine pharmaceutically acceptable salt, pharmaceutically acceptable inorganic salt, pharmaceutically acceptable organic salt, morphine hydrobromide, morphine hydrochloride, morphine mucate, morphine N-oxide, morphine sulfate, morphine acetate, morphine phosphate dibasic, morphine phosphate monobasic, morphine inorganic salt, morphine organic salt, morphine acetate trihydrate, morphine bi(heptafluorobutyrate), morphine bi(methylcarbamate), morphine bi(pentafluoropropionate), morphine bi(pyridine-3-carboxylate), morphine bi(trifluoroacetate), morphine bitartrate, morphine chlorhydrate, and morphine sulfate pentahydrate.

EXAMPLE 1

A novel therapeutic composition comprising morphine, wherein morphine is a member selected from the group consisting of morphine and morphine pharmaceutically acceptable salt is prepared as follows: first, 432 g of morphine sulfate pentahydrate, 963 g of poly(alkylene oxide) comprising a 300,000 molecular weight and 90 g of poly(vinyl pyrrolidone) having an average molecular weight of 40,000 are added to a mixing bowl and dry mixed for 10 to 12 minutes. Next, 404 g of denatured, anhydrous alcohol is slowly added to the blended composition-forming materials with continuous mixing for 15 minutes. Then, the prepared wet granulation is passed through a 20 mesh screen, and allowed to dry at room temperature of 25° C. for 18 hours, and then passes through a 16 mesh screen. The screened granulation is transferred to a planetary mixer, and with constant blending 14.9 g of calcium stearate is added to produce the therapeutic composition. The composition is compressed into tablet comprising 250 mg of the therapeutic composition consisting of 70 mg of morphine sulfate. The tablets are compressed under 10 tons of pressure to provide sustained-release morphine sulfate tablet.

EXAMPLE 2

A therapeutic composition provided by this invention comprises 50 ng to 1200 mg of a member selected from the group consisting of morphine, morphine base, morphine salt, and morphine derivative; 5 mg to 750 mg of a poly(alkylene oxide) comprising a 100,000 to 650,000 molecular weight and selected from the group consisting of poly(methylene oxide), poly(ethylene oxide), poly(propylene oxide), poly(isopropylene oxide), and poly(butylene oxide); 0.5 mg to 80 mg of poly(vinyl pyrrolidone) having a 3,000 to 350,000 average molecular weight; and 0 to 10 mg of a lubricant represented by a member selected from the group consisting of magnesium stearate, calcium stearate, potassium oleate, stearic acid, and sodium stearate. The therapeutic composition may contain other components for examples colurants, compression aids, and binders. The composition can be compressed at ⅛ to 10 ton-force, to yield an orally-administrable tablet comprising morphine sulfate.

The therapeutic composition can be dry compressed into an orally administrable tablet. For example, a mixture of dry-powder ingredients comprising morphine pharmaceutically acceptable base, or morphine pharmaceutically acceptable salt represented by hydrochloride, hydrobromide, sulfate, bisulfate, acetate, oxalate, valerate, oleate, laureate, borate, benzoate, lactate, phosphate, tosylate, titrate, maleate, fumarate, succinate, tartrate and napsylate; a tablet excipient represented by 0 to 750 mg of microcrystalline cellulose, and 5 to 750 mg of a carboxymethylcellulose such as sodium carboxymethylcellulose of 10,000 to 800,000 molecular weight; a binding agent represented by poly(vinyl pyrrolidone), hydroxypropylcellulose and hydroxypropylmethylcelluylose and gelatin; and a lubricant like stearic acid, calcium stearate, and magnesium stearate, are dried sieved and mixed with other optional components such as a surfactant and flavoring agent fed to a tablet press and the mixture compressed under force to yield dry-compressed morphine tablets for oral administration. In an optional manufacture provided by this invention, a therapeutic composition made by wet granulation or dry granulation techniques can be surrounded with a semipermeable polymeric wall comprising a cellulose acylate and an exit means for delivering morphine at a controlled-sustained rate of delivery through the exit means over time.

EXAMPLE 3

A dosage form is provided by the invention by first preparing a morphine composition wherein 1728 g of morphine sulfate pentahydrate, 3852 g of poly(ethylene oxide) possessing a 200,000 molecular weight, and 360 g of poly(vinyl pyrrolidone) having an average molecular weight of 40,000 are added to a planetary mixing bowl. Next, the dry materials were mixed for ten minutes. Then, 1616 g of denatured anhydrous ethyl alcohol is slowly added to the blended materials with continuous mixing for 15 minutes. Next, the freshly prepared wet granulation was passed through a 20 mesh screen, allowed to dry at room temperature for 20.5 hours, and passed through a 16 mesh screen. Next, the granulation was transferred to a planetary mixer, mixed and lubricated with 59.8 g of magnesium stearate.

Next, a push composition is prepared as follows: first a binder solution was prepared dry dissolving 3910 g of hydroxypropylmethylcellulose possessing an average molecular weight of 11,200 in 45,339 g of water. Next, 101 g of butylated hydroxytoluene was dissolved in 650 g of denatured anhydrous alcohol. Approximately 2.5 kg of the hydroxypropylmethylcellulose/water solution is added to the butylated hydroxytoluene/alcohol solution with continuous mixing. Next, the binder solution preparation is completed by adding the remaining hydroxypropylmethylcellulose/water solution to the butylated hydroxytoluene/alcohol solution, again with continuous mixing.

Next, 36,000 g of sodium chloride was sized using a Quadro Comil® mill, used to reduce the particle size of the sodium chloride. A fluid air mill is another mill used to size materials with a 21 mesh screen. Next, 1200 g of ferric oxide was passed through a 40 mesh screen. Then, all the screened materials, 76,400 g of pharmaceutically acceptable poly(ethylene oxide) comprising a 7,000,000 molecular weight, 2520 g of hydroxypropylmethylcellulose comprising an average molecular weight of 11,200 are added to a Glatt Fluid Bed Granulator's bowl. The bowl was attached to the granulator and the granulation process was initiated for effecting granulation. Next, the dry powders were air suspended and mixed for 10 minutes. Then, the binder solution was sprayed from 3 nozzles onto the powder. The granulating conditions were monitored during the process as follows: total solution spray rate of 800 g/rain; inlet temperature 43° C.; and process air flow of 4300 m³/hr.

While spraying the binder solution, the filter bags were shaken for 10 seconds every 1.5 minutes to unglue any possible powder deposits. At the end of the solution spraying, 45,033 g, the coated granulated particles were continued with the drying process for 35 minutes. The machine was turned off, and the coated granules were removed from the granulator. The coated granules were sized using a Quadro Comil with an 8 mesh screen. The granulation was transferred to Tote Tumbler, mixed and lubricated with 281.7 g of magnesium stearate.

Next, the morphine sulfate pentahydrate drug composition and the push composition are compressed into bilayer tablets on the Kilian® Tablet Press. First, 434 mg of the morphine sulfate pentahydrate composition is added to the die cavity and pre-compressed, then, 260 mg of the push composition is added and the layers are pressed under a pressure head of approximately 3 metric tons into a 0.700" (1.78 cm)×0.375" (0.95 cm) oval contacting layered arrangement.

The bilayered arrangements are coated with a semi-permeable wall. The wall forming composition comprises 95% cellulose acetate having a 39.8% acetyl content, and 5% polyethylene glycol having a molecular weight of 3350. The wall-forming composition is dissolved in an acetone-:water (95:5 wt:wt) cosolvent to make a 4% solids solution. The wall-forming composition is sprayed onto and around the bilayers in a 24" Vector Hi® Coater.

Next, two 30 mil (0.762 mm) exit passageways are drilled through the semi-permeable wall to connect the drug layer with the exterior of the dosage system. The residual solvent is removed by drying for 48 hours at 50° C. and 50% humidity. Next, the osmotic dosage forms are dried for 4 hours at 50° C. to remove excess moisture. The dosage form produced by this manufacture provides 28.8% morphine sulfate pentahydrate, 64.2% poly(ethylene oxide) possessing a 200,000 molecular weight, 6% poly(vinyl pyrrolidone) possessing a 40,000 molecular weight, and 1% magnesium stearate. The push composition comprises 63.675% poly-(ethylene oxide) comprising a 7,000,000 molecular weight, 30% sodium chloride, 5% hydroxypropylmethylcellulose comprising a 11,200 molecular weight, 1% ferric oxide, 0.075% butylated hydroxytoluene, and 0.25% magnesium stearate. The semipermeable wall comprises 95 wt % cellulose acetate comprising a 39.8% acetyl content, and 5.0 wt % polyethylene glycol comprising a 3350 molecular weight. The dosage form comprises two passageways, 30 mils (0.762 mm), and it had a morphine sulfate mean release rate of 5 mg/hr.

The dosage form in further embodiments can comprises 65 wt % to 100 wt % of a cellulose polymer which polymer comprises a member selected from the group consisting of a cellulose ester, cellulose diester, cellulose triester, cellulose ether, cellulose ester-ether, cellulose acylate, cellulose diacylate, cellulose triacetate, cellulose acetate butyrate, and the like. The wall can also comprise from 0 wt % to 40 wt % of a cellulose ether member selected from the group consisting of hydroxypropylcellulose and hydroxypropylmethylcellulose and from 0 wt % to 20 wt % of polyethylene glycol. The total amount of all components comprising the wall is equal to 100 wt %. Semipermeable polymers useful for manufacturing wall of dosage form are disclosed in U.S. Pat. Nos. 3,845,770; 3,916,899; 4,008,719; 4,036,228; and 4,111,201. These patents are assigned to the ALZA Corporation of Palo Alto, Calif., the assignee of this patent application.

The wall in other preferred manufacture, comprises the selectively permeable cellulose ether, ethyl cellulose. The ethyl cellulose comprises an ethoxy group with a degree of substitution, DS, of about 1.4 to 3, equivalent to 40% to 50% ethoxy content, and a viscosity range of 7 to 100 centipoise, or higher. More specifically, the wall comprises 45 wt % to 80 wt % ethyl cellulose, from 5 wt % to 30 wt % hydroxypropylcellulose, and from 5 wt % to 30 wt % polyethylene glycol, with the total weight percent of all components comprising the wall equal to 100 wt %. In another embodiment the wall comprises 45 wt % to 80 wt % of ethylcellulose, from 5 wt % to 30 wt % hydroxypropylcellulose, from 2 wt % to 20 wt % of polyvinyl pyrrolidone, with the total amount of all components comprising the wall equal to 100 wt %. The ethylcellulose polymer is known in U.S. Pat. No. 4,519,801 assigned to the ALZA Corporation of Palo Alto, Calif.

EXAMPLE 4

In the dosage forms provided by the invention, the drug composition can comprises 10 to 98 wt % morphine, morphine base, morphine salt, or morphine derivative; 10 to 80 wt % poly(alkylene oxide) possessing a 100,000 to 650,000 molecular weight or 10 to 80 wt % of a carboxymethylcellulose, such as sodium carboxymethylcellulose or potassium carboxymethylcellulose possessing a 10,000 to 400,000 molecular weight; 1 to 20 wt % poly(vinyl pyrrolidone) or hydroxypropylcellulose or hydroxypropylmethylcellulose;

and 0.25 to 10 wt % lubricant such as magnesium stearate. In the dosage form, the push composition comprises 40 to 99 wt % poly(alkylene oxide) exemplified by poly(ethylene oxide) comprising a 3,000,000 to 7,750,000 molecular weight, or 20 to 99 wt % of alkali carboxymethylcellulose comprising a 500,000 to 1,000,000 molecular weight; 0 to 80 wt % of an osmagent, also known as osmotic effective solute, represented by magnesium sulfate, sodium chloride, lithium chloride, potassium sulfate, sodium sulfate, lithium sulfate, potassium acid phosphate, mannitol, urea, inositol, magnesium succinate, tartaric acid, carbohydrates like raffinose, sucrose, glucose, lactose, fructose, sodium chloride fructose, and potassium chloride dextrose; and 0.25 to 25 wt % of a hydroxyalkylcellulose selected from the group consisting of hydroxyethylcellulose, hydroxypropylcellulose, hydroxyisopropylcellulose, hydroxybutylcellulose, hydroxypropylmethylcellulose, hydroxypropylethylcellulose, hydroxypropylbutylcellulose, which hydroxyalkylcellulose comprises a 7,500 to 75,000 molecular weight; 0 to 3 wt % ferric chloride; 0 to 3 wt % antioxidant represented by d-alpha tocopherol, dl-alpha tocopherol, d-alpha tocopherol acetate, dl-alpha-tocopherol acetate, d-alpha tocopherol acid succinate, dl-alpha tocopherol acid succinate, ascorbyl palmitate, butylated hydroxyanisole, butylated hydroxytoluene, and propyl gallate; and 0 to 3 wt % lubricant represented by magnesium stearate, calcium stearate, corn starch, potato starch, bentonite, citrus pulp, and stearic acid; with all ingredients in the push composition equal to 100 wt %, weight percent.

The expression, "exit means," for the dosage form as used, comprises means and methods suitable for the metered release of beneficial drug morphine from the dosage form. The exit means comprises at least one passageway, orifice, or the like, through the wall for communicating with morphine in the dosage form. The expression, "at least one passageway," comprises aperture, orifice, bore, pore, porous element through which the drug can migrate, hollow fiber, capillary tube, porous overlay, porous insert, and the like. The expression also includes a material that erodes or is leached from the wall in the fluid environment of use to produce least one passageway in the dosage form. Representative materials suitable for forming at least one passageway, or a multiplicity of passageways, include an erodible poly(glycolic) acid, or poly(lactic) acid member in the wall, a gelatinous filament, poly(vinyl alcohol), leachable materials such as fluid removable pore forming polysaccharides, salts, oxides, or the like. A passageway or a plurality of passageways can be formed by leaching a material such as sorbitol, lactose, fructose and the like from the wall. The passageway can have any shape such as round, triangular, square, elliptical, and the like, for assisting in the metered release of morphine from the dosage form. The dosage from can be constructed with one or more passageways in spaced apart relations, or more than one passageway on a single surface of a dosage form. Passageways and equipment for forming passageways are disclosed in U.S. Pat. Nos. 3,845,770; 3,916,899; 4,063,064 and 4,088,864. Passageways of govern size formed by leaching are disclosed in U.S. Pat. Nos. 4,200,098 and 4,285,987.

Exemplary solvents used for the present purpose comprise inorganic and organic solvents that do not adversely harm the materials and the final wall or the final compositions in the dosage form. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof, Typical solvents include acetone, diacetone alcohol, methanol, ethanol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclo-hexane, cyclo-octane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

EXAMPLE 5

Representative of another dosage form provided by this invention is as follows: first, 116.1 g of morphine sulfate pentahydrate, 81.45 g of poly(ethylene oxide) of 200,000 molecular weight, and 81.45 g of poly(ethylene oxide) of 300,000 molecular weight were blended in a blender at the lowest speed for 2 minutes. Then, 78 g of poly(vinyl pyrrolidone) of 40,000 molecular weight and 500 mL of ethanol were blended for approximately 1 hour. Then, 126 mL of the poly(vinyl pyrrolidone)/ethanol blend was slowly added to the dry ingredients while blending in the mixer at the lowest speed. The granulation was dried overnight and then passed through a 0.0333", (0.846 mm) screen. Next, 2.9 g of magnesium stearate (1% of final granulation) was blended into the granulation for 1 minute using a mixer at the lowest speed.

Next, 0.7×0.375" (17.8×9.5 mm) oval dosage forms were compressed in a press with a 1 ton compression force. The pressed layers comprised of 517 mg of the morphine granulation and 310 mg of a fluid-imbibing expanding push granulation comprising 197.6 mg of poly(ethylene oxide) having a 7,000,000 molecular weight, 93.0 mg of sodium chloride, 15.5 mg of hydroxypropylmethylcellulose of 11,200 molecular weight, 3.1 mg ferric oxide, 0.8 mg of magnesium stearate, and 0.2 mg of butylated hydroxytoluene.

The push granulation was fluid bed granulated at the 120 kg scale on the Glatt fluid-bed granulator. The binder solution was made by dissolving hydroxypropylmethylcellulose and butylated hydroxytoluene in water and ethanol. This solution was sprayed on the poly(ethylene oxide), sodium chloride, hydroxypropylmethylcellulose, and ferric oxide blend while the blend was fluidized, and granules were formed. After the granulation is dried, it is milled using a Fluid Air Mill. Finally, the lubricant, magnesium stearate, is added.

The push pull morphine sulfate dosage forms were coated on the 24" Hi Coater. Lactose cores, 0.7"×0.375" in size, were used to bring the coater load up to 10 kg. The components of the semi-permeable membrane are a 95:5 (wt:wt) mixture of cellulose acetate with a 39.8% acetyl content and polyethylene glycol with a molecular weight of 3350. These components are dissolved in a 95:5 (wt:wt) mixture of acetone and water at 4% solids. An aqueous based coating solution can also be used to apply the semi-permeable membrane to this system. Two 30 mil orifices are drilled into each system. Then, the dosage forms are dried overnight at 37 degrees Celsius to yield the dosage form.

DISCLOSURE FOR USING THE INVENTION

The invention concerns also a method for administering 50 ng to 1,200 mg of morphine to a patient, said method comprising orally admitting into the patient 50 ng to 1,200 mg of morphine selected from the group consisting of morphine and morphine salt, administered from a therapeutic composition comprising 50 ng to 1,200 mg of morphine, 5 mg to 750 mg of a poly(alkylene oxide) having a 100,000 to 650,000 molecular weight and 0.5 mg to 80 ng of poly(vinyl pyrrolidone) having a 3,000 to 350,000 molecular weight over an extended time.

The method provides additionally administering 50 ng to 1,200 mg of morphine, in the patient administered from a dosage form comprising a semipereable wall permeable to aqueous-biological fluid and impervious drug; a morphine composition, which dosage form comprises 10 to 98 wt % morphine, 10 to 80 wt % poly(alkylene oxide) possessing a 100,000 to 650,000 molecular weight, and 1 to 20 wt % poly(vinyl pyrrolidone), and a push composition compressing 40 to 99 wt % poly(alkylene oxide) comprising a 3,000,000 to 7,750,000 molecular weight, 0 to 80 wt % of an osmagent, and 0.25 to 25 wt % of a hydroxy-alkylcellulose possessing a 7,500 to 75,000 molecular weight, which morphine composition and push compositions are surrounded by the semipermeable wall; and exit means in the wall for delivering the morphine from the dosage form, by imbibing fluid through the wall into the dosage from causing the morphine composition, and causing the push composition to expand and push the morphine composition through the exit means, whereby through the combined operations of the dosage form, morphine is delivered at a therapeutically effective dose at a controlled rate over a sustained period of time.

Inasmuch as the forgoing specification comprises disclosed embodiments, it is understand what variations and modifications may be made herein, in accordance with the principles disclosed, without departing from the invention.

We claim:

1. A dosage in the form of a tablet comprising: a morphine composition layer comprising 10 wt % to 98 wt % of morphine, 10 wt % of 80 wt % of a poly(alkylene oxide) having a 100,000 to 650,000 molecular weight, and 1 wt % to 20 wt % of a poly(vinyl pyrrolidone) having a 3,000 to 350,000 molecular weight; an expandable layer comprising granules coated with hydroxypropylmethylcellulose, said granules comprising 40 wt % to 99 wt % of poly(alkylene oxide) having a 3,000,000 to 7,500,000 molecular weight, 0 wt % to 80 wt % of an osmagent, and 0.25 wt % to 25 wt % of hydroxyalkylcellulose having a 7,500 to 75,000 molecular weight.

2. The dosage form according to claim 1, wherein morphine is a member selected from the group consisting of morphine base, morphine chlorhydrate, morphine bitartrate, morphine bi(trifluoroacetate), morphine bi(pentafluoropropionate), morphine bi(methylcarbonate), morphine bi(heptafluorbutyrate), morphine phosphate monobasic, morphine acetate, morphine n-oxide, morphine sulfate, morphine n-oxide, morphine oleate, morphine methylbiomide, morphine mutate, morphine hydrochloride, and morphine hydrobiomide.

3. A method for administering 50 ng to 1,200 mg of morphine to a human, which method comprises admitting orally into the gastrointestinal tract of the human 50 ng to 1,200 mg of morphine that is administered from a dosage in the form of a tablet comprising a morphine layer comprising 10 wt % to 98 wt % of morphine, 10 wt % to 80 wt % of poly(alkylene oxide) having a 100,000 to 650,000 molecular weight and 1 wt % to 20 wt % of poly(vinyl pyrrolidone) having a 3,000 to 350,000 molecular weight, a hydrogel layer comprising coated granules comprising 40 wt % to 99 wt % of poly(alkylene oxide) having 3,000,000 to 7,500,000 molecular weight, and 0 wt % to 80 wt % of an osmagent, said coat comprising 0.25 wt % to 25 wt % of a hydroxyalkylcellulose possessing a 7,500 to 75,000 molecular weight, and a semipermeable cellulose acetate polymeric composition surrounding the morphine layer and the hydrogel layer.

* * * * *